(12) United States Patent
Simhambhatla

(10) Patent No.: US 6,890,395 B2
(45) Date of Patent: May 10, 2005

(54) MEDICAL DEVICE FORMED OF ULTRAHIGH MOLECULAR WEIGHT POLYOLEFIN

(75) Inventor: Murthy V. Simhambhatla, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/438,525

(22) Filed: May 15, 2003

(65) Prior Publication Data

US 2003/0194520 A1 Oct. 16, 2003

Related U.S. Application Data

(60) Division of application No. 09/713,642, filed on Nov. 14, 2000, now Pat. No. 6,602,224, which is a continuation-in-part of application No. 09/470,056, filed on Dec. 22, 1999, now Pat. No. 6,428,506.

(51) Int. Cl.[7] .......................... B29C 47/88; B29C 53/40; B29C 53/42
(52) U.S. Cl. ........................ 156/218; 264/127; 264/291; 264/323; 264/345
(58) Field of Search .......................... 156/218; 264/127, 264/291, 323, 345

(56) References Cited

U.S. PATENT DOCUMENTS

| | | |
|---|---|---|
| 3,426,754 A | 2/1969 | Bierenbaum et al. |
| 3,679,538 A | 7/1972 | Druin et al. |
| 3,953,566 A | 4/1976 | Gore |
| 3,962,153 A | 6/1976 | Gore |
| 4,187,390 A | 2/1980 | Gore |
| 4,279,245 A | 7/1981 | Takagi et al. |

(Continued)

FOREIGN PATENT DOCUMENTS

| | | |
|---|---|---|
| EP | 0 253 513 | 1/1988 |
| EP | 0 267 719 | 5/1988 |
| EP | 0 313 263 | 4/1989 |
| EP | 0 376 503 | 7/1990 |
| WO | WO91/01210 | 2/1991 |
| WO | WO 91/01210 | * 2/1991 |

OTHER PUBLICATIONS

Keller, A., *Unusual Orientation Phenomena in Polyethylene Interpreted in Terms of the Morphology, Journal of Polymer Science*, vol. XV, pp. 31–49, 1955.
Breslow et al. "Soluble Catalysts for Ethylene Polymerization" J. Am. Chem. Soc. 81:81–86 (1959).
Hill, M.J., et al. *Direct Evidence for Distinctive, Stress–Induced Nucleus Crystals in the Crystallization of Oriented Polymer Melts, Journal of Micromolecular Science*, pp. 153–169, Mar. 1969.
Sprague, B.S., *Relationship of Structure and Morphology to Properties of "Hard" Elastic Fibers and Films, Journal of Macromolecular Science*, vol. B8(1–2), pp. 157–187, 1973.
van Hutten, P.F. et al., *Shish–Kebab as an Intermediate Morphology in Gel–Spinning/Hot–Drawing of Polyethylene, Polymer Communications*, vol. 24, pp. 237–240, 1983.

(Continued)

Primary Examiner—Sharon Kennedy
(74) Attorney, Agent, or Firm—Fulwider, Patton, Lee & Utecht LLP

(57) ABSTRACT

Medical devices having at least a component, such as a catheter balloon, stent cover and vascular graft, formed of ultrahigh molecular weight polyolefin, such as ultrahigh molecular weight polyethylene. The device component is formed from ultrahigh molecular weight polyethylene that has been processed so that it is microporous and has an oriented node and fibril structure. The device component expands compliantly at low strains and are substantially less compliant at higher strains. The invention also comprises methods for making such medical devices, including the steps of compacting a polyethylene powder and deforming it to impart the oriented structure.

12 Claims, 1 Drawing Sheet

U.S. PATENT DOCUMENTS

| | | | |
|---|---|---|---|
| 4,384,023 A | | 5/1983 | Okamura et al. |
| 4,413,101 A | | 11/1983 | Schmidt et al. |
| 4,422,993 A | | 12/1983 | Smith et al. |
| 4,482,516 A | | 11/1984 | Bowman et al. |
| 4,536,536 A | | 8/1985 | Kavesh et al. |
| 4,655,769 A | | 4/1987 | Zachariades |
| 4,668,557 A | | 5/1987 | Lakes |
| 4,833,172 A | | 5/1989 | Schwarz et al. |
| 4,876,049 A | | 10/1989 | Aoyama et al. |
| 5,213,363 A | | 5/1993 | Fukumori et al. |
| 5,335,675 A | | 8/1994 | Wheeler et al. |
| 5,374,473 A | | 12/1994 | Knox et al. |
| 5,433,909 A | | 7/1995 | Martakos et al. |
| 5,499,973 A | | 3/1996 | Saab |
| 5,569,196 A | | 10/1996 | Muni et al. |
| 5,752,934 A | | 5/1998 | Campbell et al. |
| 5,753,358 A | | 5/1998 | Korleski |
| 5,782,903 A | | 7/1998 | Wiktor |
| 5,788,626 A | | 8/1998 | Thompson |
| 6,120,477 A | | 9/2000 | Campbell et al. |
| 6,165,166 A | | 12/2000 | Samuelson et al. |
| 6,238,408 B1 | | 5/2001 | Kawabata et al. |
| 6,344,045 B1 | | 2/2002 | Lim et al. |
| 6,395,208 B1 | | 5/2002 | Herweck et al. |
| 6,761,786 B2 | * | 7/2004 | Simhambhatla et al. .... 156/218 |
| 2003/0216805 A1 | * | 11/2003 | Edwin et al. .............. 623/1.15 |
| 2004/0157024 A1 | * | 8/2004 | Colone ...................... 428/36.9 |
| 2004/0170782 A1 | * | 9/2004 | Wang et al. ............... 428/35.2 |

OTHER PUBLICATIONS

Smook, Jan, et al., *Elastic Flow Instabilities and Shish–Kebab Formation During Gel–Spinning of Ultra–High Molecular Weight Polyethylene*, Journal of Materials Science, vol. 19, pp. 31–43, 1984.

van Hutten, P.F. et al., *The Deformation Behaviour of Polyethylene Shish–Kebab Produced by Stirring–Induced Crystallization*, Colloid and Polymer Science, vol. 262, pp. 521–525, 1984.

van Hutten, P.F. et al., *The Plastic Deformation of Ultra–High Molecular Weight Polyethylene*, Journal of Materials Science, vol 20, pp. 1556–1571, 1985.

Harvey L. Stein, UltraHigh Molecular Weight Polyethlenes (UHMWPE), Engineered Materials Handbook—vol. 2: Engineering Plastics, 167–171, (1988).

Caddock et al. "Microporous materials with negative Poisson's ratios: 1. Microstructure and mechanical properties", Journal of Physics D: Applied Physics,22(12):1877–1882 (1989).

Murthy, N.S. et al.; *Structural Changes Prior to Melting in Extended–Chain Polyethylene Fibres*, Polymer Communications, vol. 31, pp. 50–52, 1990.

Chien et al. "Ethylene–Hexene Copolymerization by Heterogeneous and Homogeneous Ziegler–Natta Catalysts and the "Comonomer" Effect" Journal of Polymer Science: Part A: Polymer Chemistry 31:227–237 (1993).

Zucchini et al. "Behaviour of [Ti$_2$(OEt)$_8$Cl]$_2$Mg$_2$($\mu$–Cl)$_2$ as a catalyst component in the Ziegler–Natta polymerization of alpha.–olefins and diolefins" Journal of Molecular Catalysis 82:45–46 (1993).

* cited by examiner

U.S. Patent  May 10, 2005  US 6,890,395 B2
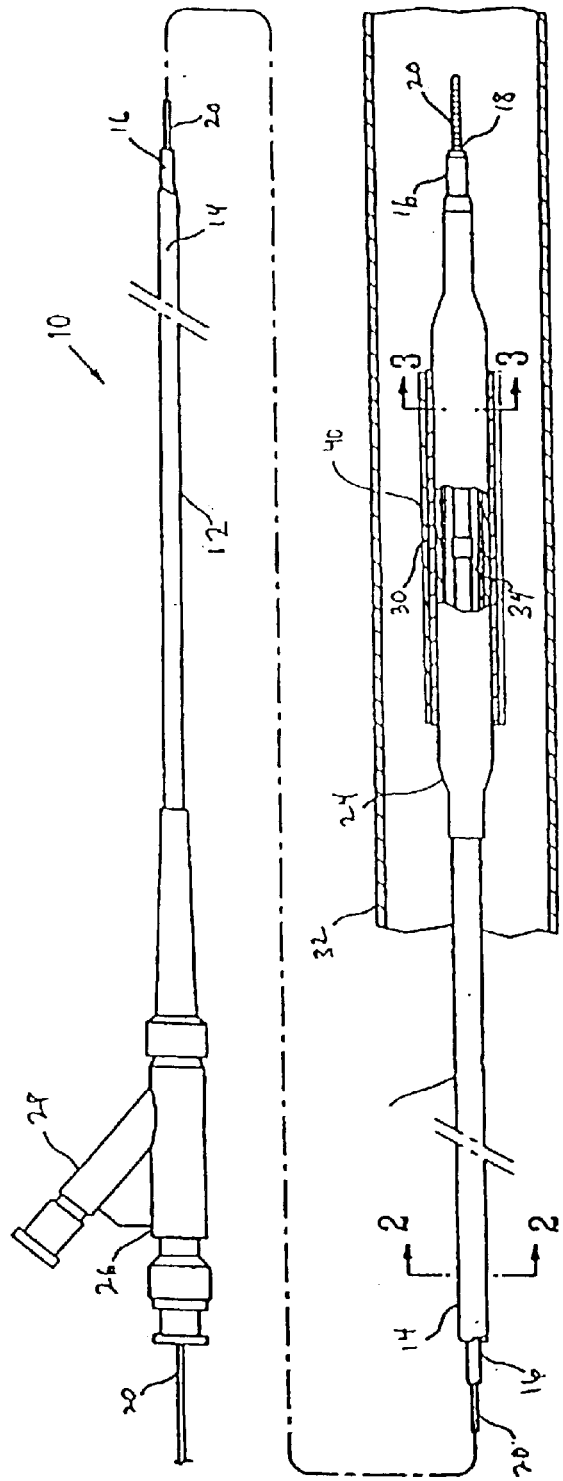
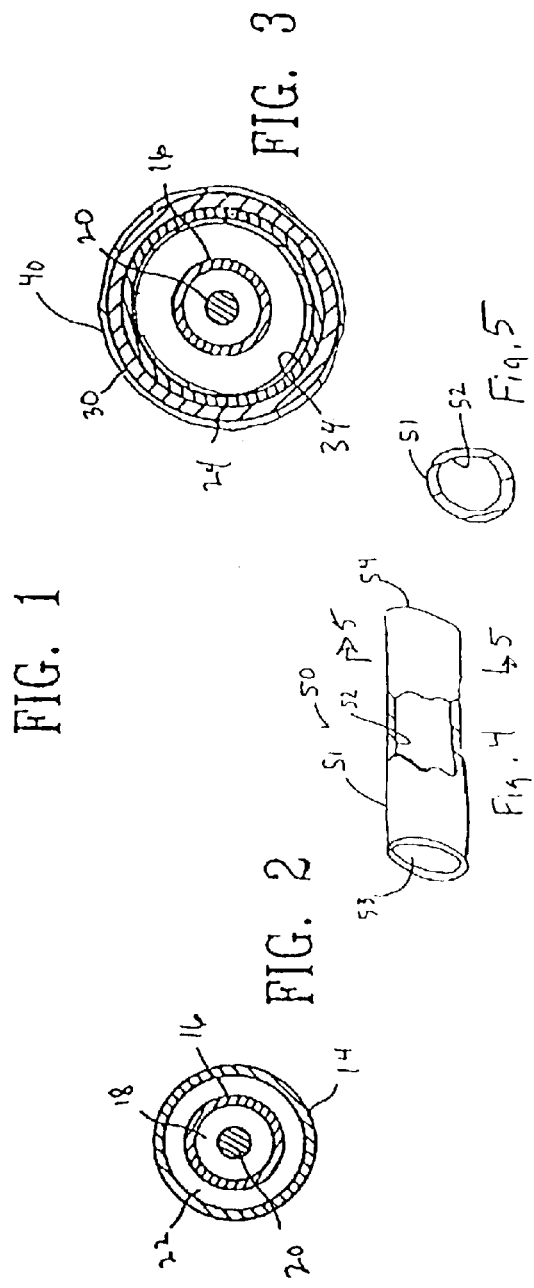
FIG. 1
FIG. 2
FIG. 3
FIG. 4
Fig. 5

MEDICAL DEVICE FORMED OF ULTRAHIGH MOLECULAR WEIGHT POLYOLEFIN

This application is a divisional application of application Ser. No. 09/713,642, filed Nov. 14, 2000, now U.S. Pat. No. 6,602,224, which is a continuation-in-part application of application Ser. No. 09/470,056, filed Dec. 22, 1999, now U.S. Pat. No. 6,428,506 entitled Medical Device Formed of Ultrahigh Molecular Weight Polyethylene, incorporated herein by reference in its entirety.

BACKGROUND OF THE INVENTION

This invention generally relates to medical devices, and particularly to balloon catheters, stent covers, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as DACRON may be implanted in vessels to strengthen or repair the vessel, or used in an anastomosis procedure to connect vessels segments together.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy and cross lesions in the uninflated state. The balloon compliance is chosen so that the balloon will have a desired amount of expansion during inflation. Compliant balloons, for example balloons made from materials such as polyethylene, exhibit substantial stretching upon application of internal pressure. Noncompliant balloons, for example balloons made from materials such as PET, exhibit relatively little stretching during inflation, and therefore provide controlled radial growth in response to an increase in inflation pressure within the working pressure range.

For many applications, intravascular catheter balloons should be substantially noncompliant once expanded to a working diameter. Further, catheter balloons should also be formed from relatively strong materials in order to withstand the pressures necessary for various procedures without failing. Typically, such characteristics require the use of a material that does not stretch appreciably, which consequently necessitates that the balloon material be folded around the catheter shaft prior to inflation. However, it can be desirable to employ balloons that are not folded prior to inflation, but which are instead expanded to the working diameter from a generally cylindrical or tubular shape having a nominal diameter that conforms to the catheter shaft. Such designs may be used for formed-in-place angioplasty balloons and stent delivery balloons. Prior art formed-in-place balloons have suffered from problems such as insufficient strength, poor control over expansion, and significantly complicated processing during catheter manufacturing.

It would be a significant advance to provide a catheter balloon, and other expandable members such as stent covers, and vascular grafts, with improved processing and expansion characteristics.

SUMMARY OF THE INVENTION

This invention is directed to medical devices, and particularly intracorporeal devices for therapeutic or diagnostic uses, having at least a component formed of ultrahigh molecular weight polyolefin (UHMW polyolefin). In a presently preferred embodiment, the UHMW polyolefin is an ultrahigh molecular weight polyethylene (UHMW polyethylene). A presently preferred embodiment is directed to UHMW polyolefin which is microporous, and having a node and fibril microstructure comprising nodes interconnected by fibrils.

One embodiment of the invention comprises an expandable member such as a balloon for an intraluminal catheter, formed at least in part of the UHMW polyolefin, such as UHMW polyethylene. In another embodiment of the invention, a stent delivery system comprising a balloon catheter and a stent mounted on the balloon has a component, such as the catheter balloon or a stent cover, which is formed at least in part of the UHMW polyolefin, such as UHMW polyethylene. Another embodiment of the invention comprises a vascular graft formed at least in part of the UHMW polyolefin, such as UHMW polyethylene. The terminology vascular graft as used herein should be understood to include grafts and endoluminal prostheses, such as those surgically attached to vessels, as for example in vascular bypass or anastomosis, or implanted within vessels, as for example in aneurysm repair or at the site of a balloon angioplasty or stent deployment. Although discussed below primarily in terms of a balloon catheter having a balloon formed of UHMW polyethylene, the invention should be understood to include other medical devices and particularly intracorporeal devices for a therapeutic or diagnostic purpose, such as stent covers and vascular grafts formed of UHMW polyolefin, such as UHMW polyethylene. Additionally, although discussed primarily in terms of UHMW polyethylene, it should be understood that the invention applies as well to UHMW polyolefins in general, and to other materials having a node and fibril microstructure such as polypropylene, nylon, and expanded polytetrafluoroethylene.

The UHMW polyethylene has a molecular weight which is higher than the molecular weight of high molecular weight polyethylenes, and which is about 2 million to about 10 million grams/mole, preferably about 3 million to about 6 million grams/mole. Unlike high molecular weight polyethylenes, which generally have a molecular weight of about 400,000 to about 600,000 grams/mole, the UHMW polyethylene is difficult to melt process. Balloons formed from this material exhibit compliant expansion at relatively low strains and exhibit substantially less compliance at higher strains.

The node and fibril structure of the UHMW polyethylene causes it to exhibit essentially compressible deformation at relatively small strains, with a low Young's modulus in tension for the compressed material. At high strains, the UHMW polyethylene balloons of the invention preferably exhibit low compliance due to rearrangement in the microstructure. Embodiments of the invention suited to intravascular applications preferably exhibit compliant radial expansion of about 70% to about 450%, and more particularly 100% to about 400%, of the uninflated diameter, at pressures up to about 6 to about 8 atm. Once expanded, the balloons exhibit relatively low compliance at pressures above about 8 atm and can have a burst pressure of at least about 18 atm. In one embodiment, the UHMW polyethylene exhibits microstructural rearrangement and the balloon exhibits low compliance in the working pressure range with a radial expansion of about 5% to about 20%, and preferably less than about 15% of the uninflated diameter of the balloon, at inflation pressures of about 6 atm to about 18 atm. In one embodiment, the UHMW polyethylene exhibits a negative Poisson ratio. For stent delivery applications, the UHMW polyethylene preferably has a foam-like compressible state at low strains so that the stent can be crimped onto the balloon with good retention.

One aspect of the invention is directed to a noninflated balloon comprising ultrahigh molecular weight polyolefin in a compressed configuration having a reduced porosity relative to the ultrahigh molecular weight polyolefin in a noncompressed configuration. In one embodiment, the balloon formed of UHMW polyolefin, such as UHMW polyethylene, is compressed in the radial direction of the balloon, to provide a reduced profile medical device component. In another embodiment, the balloon formed of UHMW polyolefin, such as UHMW polyethylene, is compressed in the axial direction of the balloon, to provide reduced axial lengthening during radial expansion of the medical device component formed therefrom.

In another embodiment, the UHMW polyolefin, such as UHMW polyethylene, is compressed before being formed into a balloon, to provide a balloon exhibiting improved stress/strain curve response. The UHMW polyolefin compressed before being formed into a balloon is preferably compressed in the direction of the fibrils of the material, i.e., in the direction of the deformation which imparted the node and fibril structure to the material, while the thickness of the material is held constant. However, in an alternative embodiment, the UHMW polyolefin is compressed perpendicular or substantially perpendicular to the direction of the fibrils. The stress/strain curve response of the compressed UHMW polyolefin is characterized by a sudden increase of stress at increased strain, which allows for the construction of a balloon having desired expansion characteristics with a compliant radial expansion at initial inflation pressures and relatively low compliance at higher inflation pressures. Thus, the compressed UHMW polyethylene exhibits an improved substantial or compliant expansion upon inflation to an internal pressure within a first pressure range, and substantially less expansion within a second pressure range higher than the first pressure range. The compressed material provides a wingless balloon that can provide the desired radial compliance characteristics without excessive balloon length increase or shortening during inflation of the balloon. The shape of the stress/strain curve of the resulting compressed UHMW polyethylene material will depend on factors such as porosity of the material before compression, compression conditions, fibril length, node size and node aspect ratio, ram extrusion conditions, material deformation or orientation conditions, heat set conditions, and the balloon construction characteristics such as winding angle. The compressed UHMW polyethylene is particularly useful for a stent deploying balloon, due to the lack of wings on the unexpanded balloon. In conventional stent deploying balloons, the folded balloon wings of the unexpanded balloon would unfold during inflation of the balloon, resulting in nonuniform expansion of the stent mounted on the unexpanded balloon.

Balloon catheters of the invention generally comprise an elongated shaft with at least one lumen and balloon formed of UHMW polyolefin such as UHMW polyethylene on a distal shaft section with an interior in fluid communication with the shaft lumen. The balloon catheters of the invention may be configured for a variety of uses, such as angioplasty or stent delivery. A stent delivery catheter employs a balloon having the characteristics of the invention to deploy the stent. Preferably, the oriented polyethylene exhibits a foam-like compressible state at low strains, facilitating crimping of the stent onto the balloon with improved stent retention. In accordance with the invention, the stent may be provided with a stent cover generally comprising a tubular sheath formed of the UHMW polyethylene and configured to be disposed on an outer and/or inner surface of the stent and implanted with the stent in the patient's vessel.

Vascular grafts of the invention generally comprise a tubular body formed of the UHMW polyolefin such as UHMW polyethylene. The vascular graft is configured to be implanted in a patient, and may be used for a variety of procedures including anastomosis, bypass surgery, implantation within a vessel lumen to reduce restenosis, and aneurysm repair.

The invention also comprises methods of forming a medical device component such as a balloon, stent cover or vascular graft, from microporous polyolefin such as polyethylene having an oriented node and fibril structure. Generally, the method comprises the steps of compacting ultrahigh molecular weight polyethylene powder into a billet, deforming the compacted polyethylene to render the polyethylene microporous and to impart an oriented node and fibril structure to the polyethylene, and forming the medical device component from the polyethylene. Optionally, the powder can be sintered prior to deformation. Also optionally, the oriented polyethylene can be heat set.

Preferably, a tubular medical device component such as a balloon may be formed by wrapping a film or sheet of the oriented polyethylene around a mandrel to form a tube and then heat fusing the polyethylene layers together, or by directly producing an oriented tubular member.

The medical devices such as catheter balloons, stent covers, and vascular grafts of the invention have improved performance due to the UHMW polyolefin such as UHMW polyethylene which is microporous, biocompatible, and biostable, and which has excellent mechanical properties. Further, UHMW polyethylene is more resistant to electron-beam (i.e., e-beam) degradation than expanded polytetrafluoroethylene (i.e., ePTFE) which degrades when exposed to e-beams, making e-beam sterilization more of an option than with ePTFE. Medical devices such as balloons of this invention can be expanded compliantly to their working diameter but exhibit substantially less compliance at greater pressures, providing control over expansion even at pressures suitable for conventional intravascular procedures such as angioplasty or stent delivery. Further, the formed-in-place balloons of the invention have sufficient strength to provide desired safety to conventional intravascular procedures. UHMW polyethylene also facilitates device manufacture. because the processing temperatures for polyethylene are relatively low, and the polyethylene can be readily attached with adhesives or heat bonded using tie layers to other device components. Thus, bonding to other device components is easier than with ePTFE.

These and other advantages of the invention will become more apparent from the following detailed description when taken in conjunction with the accompanying exemplary drawings.

BRIEF DESCRIPTION OF THE DRAWINGS

FIG. 1 is an elevational view, partially in section, of a balloon catheter for delivering a stent that embodies features of the invention.

FIG. 2 is a transverse cross-section of the catheter shown in FIG. 1 taken at line 2—2.

FIG. 3 is a transverse cross-section of the catheter shown in FIG. 1 taken at line 3—3, showing the stent disposed over the inflatable balloon.

FIG. 4 is an elevational view, partially in section, of a vascular graft or stent cover which embodies features of the invention.

FIG. 5 is a transverse cross-section of the graft or cover shown in FIG. 4, taken along lines 5—5.

DETAILED DESCRIPTION OF THE INVENTION

FIGS. 1–3 illustrate an over-the-wire type stent delivery balloon catheter 10 embodying features of the invention. Catheter 10 generally comprises an elongated catheter shaft 12 having an outer tubular member 14 and an inner tubular member 16. Inner tubular member 14 defines a guidewire lumen 18 adapted to slidingly receive a guidewire 20. The coaxial relationship between outer tubular member 14 and inner tubular member 16 defines annular inflation lumen 22. An inflatable balloon 24 disposed on a distal section of catheter shaft 12 having a proximal end sealingly secured to the distal end of outer tubular member 14 and a distal end sealingly secured to the distal end of inner tubular member 16 so that its interior is in fluid communication with inflation lumen 22. An adapter 26 at the proximal end of catheter shaft 12 is configured to direct inflation fluid through arm 28 into inflation lumen 22 and provide access to guidewire lumen 18.

In the embodiment illustrated in FIG. 1, an expandable stent 30 is mounted on balloon 24. The distal end of catheter may be advanced to a desired region of a patient's body lumen 32 in a conventional manner and balloon 24 may be inflated to expand stent 30, seating it in the lumen.

In the embodiment illustrated in FIG. 1, the balloon 24 has a layer 34 formed from an elastomeric material, such as polyurethane elastomers, silicone rubbers, styrene-butadiene-styrene block copolymers, and polyamide block copolymers, and the like. In a preferred embodiment, elastomeric layer 34 is on the interior of balloon 24, although in other embodiments it may be on the exterior or the balloon 24. Elastomeric layer 34 expands elastically to facilitate deflation of the balloon 24 to its preinflation diameter and shape, and can also limit or prevent leakage of inflation fluid through the microporous polyethylene.

Balloon 24 is formed at least in part of a UHMW polyethylene. Preferably, the UHMW polyethylene has a molecular weight of about 3 million to about 6 million. Suitable UHMW polyethylenes are available from Hoechst Celanese, and described in Ultrahigh Molecular Weight Polyethylenes (UHMWPE), Engineered Materials Handbook, Vol. 2: Engineering Plastics, H. L. Stein, and WO 91/01210, incorporated by reference herein in its entirety. Presently preferred UHMW polyethylenes are classified by molecular weight determinations detailed in ASTM (American Society for Testing and Methods) D 1601 and D 4020. In a presently preferred embodiment, the UHMW polyethylene is processed so that it is microporous and exhibits an oriented structure comprising nodes interconnected by fibrils. The microporous UHMW polyethylene with an oriented node and fibril microstructure has a porosity of about 20% to about 90%, and an internodal distance, also expressed as fibril length, of about 5 $\mu$m to about 200 $\mu$m. Examples of microporous UHMW polyethylenes, having a node and fibril microstructure, and a suitably high orientation with an anisotropic structure or at least significant anisotropy in the structure, are described in WO 91/01210, incorporated by reference herein in its entirety. As described in WO 91/01210, such UHMW polyethylene materials may exhibit a negative Poisson ratio. Balloons formed from this material exhibit compliant expansion at relatively low strains and exhibit substantially less compliance at higher strains. For example, in a presently preferred embodiment, balloon 24 expands compliantly by about 70% to about 450% of the uninflated diameter at pressures of about 6 to about 8 atm. Once expanded, the balloon 24 is relatively noncompliant at pressures greater than about 8 atm, up to the burst pressure of the balloon which preferably is at least about 18 atm.

In the embodiment illustrated in FIG. 1, a stent cover 40 formed of the UHMW polyethylene is disposed on an outer surface of the stent 30. As discussed above, the UHMW polyethylene forming the stent cover 40 can be processed to be microporous with a node and fibril microstructure. Stent cover 40 is secured to the surface of the stent 30 before the stent is introduced into the patient's vasculature, and expanded, together with the stent, to implant the stent and stent cover thereon in the vessel lumen. Stent cover 40 secured to the stent has a generally tubular structure conforming to a surface of the stent. In the presently preferred embodiment illustrated in FIG. 1, the stent cover 40 extends the length of the stent 30. However, in alternative embodiments the stent cover may have a length longer than or shorter than a length of the stent. The stent cover 40 length may be selected to fit a variety of conventionally sized stents, with a typical diameter of about 2 mm to about 10 mm. The stent cover 40 wall thickness is typically about 20 μm to about 400 μm, preferably about 40 μm to about 100 μm. The stent cover 40 provides a biocompatible, biostable surface on the stent, and reduces plaque prolapse through the stent struts. A stent cover may be provided on an inner surface of the stent (not shown).

In another embodiment of the invention illustrated in FIG. 5, vascular graft 50 comprises a tubular body 51 having a lumen 52 therein, formed of an UHMW polyethylene. Ports 53,54 are at either end of the graft 50. As discussed above the UHMW polyethylene can be processed to be microporous with a node and fibril microstructure. The graft is configured for being implanted in the patient, and it may be expanded into place within a vessel or surgically attached to a vessel, such as at a free end of a vessel. The graft 50 length is generally about 4 to about 80 mm, and more specifically about 10 to about 50 mm, depending on the application, and wall thickness is typically about 40 μm to about 2000 μm, preferably about 100 μm to about 1000 μm. The diameter is generally about 1 to about 35 mm, preferably about 3 to about 12 mm, depending on the application.

A process of forming the microporous node and fibril structure of the UHMW polyethylene generally comprises compacting polyethylene powder into a billet and then deforming the billet through a die and orienting the extrudate to impart the node and fibril structure. The step of compacting the polyethylene powder can by any suitable means including the presently preferred embodiments of applying pressure, with or without additional heat, or forming a slurry with a lubricating medium and then compacting the slurry into a billet. The lubricating medium is typically evaporated from the slurry after the extrusion of the billet through a die as is discussed below to impart the oriented node and fibril structure. For extrusion without a mineral oil lubricating medium, the polymer billet may optionally be sintered at temperatures exceeding the crystalline melting point of the polymer. After being compacted, the UHMW polyethylene is then deformed to impart the oriented node and fibril structure. Typically, the polyethylene is deformed by extrusion through a die followed by uniaxial or biaxial stretching of the extrudate. The deformation step may be performed either at ambient or elevated temperatures. In one preferred embodiment, sintered polyethylene is ram extruded at ambient temperature to form a sheet of material, which is then stretched, uniaxially or biaxially, to orient the structure. Optionally, the stretched material can be heat set. The processing of the polyethylene also renders it microporous, and the amount of stretch experienced by the material controls the distance between the nodes and the corresponding fibril length.

The size and shape of the UHMW polyethylene particles of the UHMW polyethylene powder can be chosen to influence the node and fibril structure and optimize the properties of the resulting material. For example, the particle morphology determines the coarseness of the node and fibril structure and the ease of fibrillation during the deformation of the billet through a die. In a presently preferred embodiment, the UHMW polyethylene particles used to prepare the compacted polyethylene comprises an aggregate of primary particles. The aggregate has a diameter of about 100 μm to about 700 μm, preferably about 200 μm to about 400 μm, in size and is composed of aggregated or fused primary UHMW polyethylene particles having a particle size of about 0.1 μm to about 40 μm, and preferably about 0.1 μm to about 20 μm. A suitable aggregate UHMW polyethylene is grade GUR 2122, available from Ticona. Nonaggregated UHMW polyethylene particles having a particle size of less than about 10 μm may be used to make the node and fibril structure materials, provided handling and safety problems associated with such fine particles are avoided.

The synthesis of UHMW polyethylene is known to occur by Ziegler-Natta catalysis using a transition metal catalyst such as titanium, chromium or zirconium, and a co-catalyst such as aluminum. The nature of the catalyst and the order of the addition of the catalyst and co-catalyst affects the morphology of the resulting polymer. To synthesize material comprising an aggregate of a primary particle as discussed above, preferably a suspension polymerization of ethylene is used with a catalyst such as biscyclopentadienyl titanium dichloride, biscyclopentadienylzircomium dichloride, or cyclopentadienyl zirconium trichloride, and a co-catalyst such as trialkylaluminum, soluble in an alkane medium such as heptane or hexane. The trialklyaluminum co-catalysts include triethyl aluminum, tri-isopropylaluminum, and tributylaluminum. The synthesis of UHMW polyethylene by Ziegler-Natta Catalysis is described in D. Breslow et al., J. Am. Chem. Soc., 31, 81–86 (1959), J. Chien et al., J. Polym. Sci. Polym. Chem., 31, 227–237 (1993), and U. Zucchini et al., J. Molec. Cat., 82, 45–56 (1993), incorporated in their entireties by reference herein. An open aggregate structure can be formed by the control of the polymerization rate, with use of a particular temperature and catalyst, which affects the particle stability and dynamics of aggregation.

One presently preferred method of forming the UHMW polyethylene generally comprises preparing a homogeneous paste of UHMW polyethylene in a low boiling mineral oil. The paste is then compacted into a billet by applying pressure and optionally applying heat. The billet is then loaded into a ram extruder and a tube or film is extruded. The extrusion may be done at room temperature, or the temperature may be elevated. The oil is then evaporated from the UHMW polyethylene by heating the film to a temperature not exceeding the crystalline melting point of the UHMW polyethylene. The film or tube is then uniaxially or biaxially oriented to produce the oriented node and fibril structure. The oriented tube may then optionally be heat set at temperatures just above the melting point of UHMW polyethylene, which has a crystalline melting point of about 130–140° C.

Another presently preferred process comprises compacting UHMW ethylene particles into a billet at temperatures below the crystalline melting point of the polymer. Preferably, this step would be done at about 100° C. to about 120° C. The pressure applied is about 0.01 GPa to about 0.08 Gpa, preferably about 0.01 GPa to about 0.1 GPa. The billet is then sintered at temperatures above the crystalline melting point of the polymer without applying any pressure. This step is completed at a preferred temperature of about 130° C. to about 160° C. The sintered billet is extruded through a film or annular die in a ram extruder. The UHMW polyethylene is then optionally oriented and heat set as described above.

Generally, the balloons of the invention are formed from a film of stretched material. The material is wrapped around a mandrel to form a tube and then heated to fuse the wrapped material together. The resulting tubular member may be secured to the conventional catheter components by laser bonding or plasma treatment followed by adhesive bonding.

In one embodiment, the UHMW polyethylene material having a node and fibril structure is further processed by compressing the material or otherwise reducing the porosity of the material. After the polyethylene powder, which was previously compacted, is deformed or stretched to impart a node and fibril structure, the compressing force is applied to form the compressed microporous UHMW polyethylene having a reduced porosity. The material is compressed without destroying the node and fibril structure of the UHMW polyethylene. Thus, the compressed UHMW polyethylene material does not have to be restretched or redeformed to recreate the node and fibril structure. Depending on the desired result, the material is compressed either before or after being formed into a balloon or other tubular medical device component. The material is preferably heated in the compressed state, so that the material is sintered, and the dimensions of the compressed material will not change upon removal of the compressive force. The elevated temperature is sufficient to cause the material to remain in the reduced porosity state from the compression at least until the balloon is inflated. The compressing force reduces the porosity and the pore size of the material. In one embodiment, expansion of the balloon results in the porosity of the UHMW polyethylene returning to the precompression porosity value. A compressing force sufficient to reduce the porosity to about 20% to about 60% for a UHMW polyethylene having an original (precompressed) porosity of about 40% to about 90% is used.

In one embodiment, the material is formed into a balloon and then is radially compressed (i.e., in the radial direction of the tubular balloon), in order to reduce the profile of the material and consequently provide a low profile balloon formed from the material. Preferably, the entire length of the balloon material is radially compressed. However, only a section of the balloon material may be exposed to the radially compressing force. The radially compressing force may be applied at one time to the entire length of the balloon material, or alternatively, to multiple short sections of the balloon material in turn. The material is heated as the radially compressing force is applied. For example, the wrapped material may be heated to fuse the material and form the balloon, and then the compressing force applied to the balloon either while at the elevated fusing temperature or after cooling and then reheating to an elevated temperature. The radially compressing force reduces the thickness of the microporous UHMW polyethylene by about 10% to about 50%.

In one embodiment, the material is formed into a balloon and then the balloon is axially compressed, (i.e., along a longitudinal axis of the tubular balloon), such that the balloon radially expands during inflation without significant shortening of the length of the balloon. In a presently preferred embodiment, in the embodiment in which the material is helically wrapped on a mandrel and fused to form the tubular balloon, the tubular balloon is at least axially compressed. Thus, the balloon axially shrinks during radial expansion by less than about 15%, preferably less than about 10%, of the length of the balloon, compared with a nonaxially compressed balloon which is believed to shrink by greater than about 15% to about 30% of the length of the balloon. For axial compression, the tube is typically disposed on a mandrel and the length of the tube shortened by displacing a member that is coaxial with the mandrel. The compressed material is heated in the compressed state. For example, the ends of the axially compressed material are fixed by tightening a wire or a fastening member thereto, and the material is then heated in the axially compressed condition to an elevated temperature at or above the crystalline melting temperature of the material, or of about 130° C. to about 170° C. for UHMW polyethylene. The axially compressing force reduces the length of the microporous UHMW polyethylene by about 10% to about 50%.

In another embodiment, the material is compressed before being formed into a balloon, such that the resulting balloon formed from the compressed material has a hybrid compliant curve in which it has substantial expansion within a first pressure range and substantially less expansion within a second pressure range greater than the first pressure range. In one embodiment, the compressing force is applied to the material in a direction parallel to or substantially parallel to the direction(s) of deformation which imparted the node and fibril structure, while the radial direction or thickness of the material is restrained to a constant value. The terminology substantially parallel should be understood to mean closer to parallel to than perpendicular to the direction of deformation which imparted the node and fibril structure. Preferably, the compression is in the direction of the fibrils, and the fibrils are oriented along the hoop direction, i.e., circumferentially, of the resulting balloon. In order to apply the compressing force parallel to the direction of the fibrils while holding the thickness of the material constant, a sheet of material may be placed flat between two plates and the ends of the materials compressed inwardly towards oneanother. The compressed material is heated in the compressed state. The length of the material is decreased, and in a presently preferred embodiment to about 10% of the original length, and the thickness does not increase due to the restraining force of the plates. In an alternative embodiment, the material used to make a balloon having a hybrid compliant curve is produced by applying the compressing force perpendicular or substantially perpendicular to the direction of deformation which imparted the node and fibril structure, and the thickness of the material thus reduced. The compressed UHMW polyethylene balloon material provides a balloon having a compliance of about 0.25 mm/atm to about 0.75 mm/atm within a first pressure range of about 1 atm to about 6–8 atm, and a compliance of about 0.015 mm/atm to about 0.07 mm/atm within a second pressure range of about 7–9 atm to about 16–18 atm.

While discussed in terms of a balloon, it should be understood that the compression of the UHMW polyethylene discussed above applies to the other embodiments of the invention, including the vascular graft and stent cover. Additionally, while discussed primarily in terms of UHMW polyethylene, the compression which results in reduced porosity may be used on other polymeric materials having a node and fibril structure, including for example expanded polytetrafluoroethylene, nylon, and polypropylene. Moreover, while discussed primarily in terms of a radially expandable component for a medical device having a node and fibril microstructure, with an unexpanded compressed configuration having a reduced porosity relative to the material in a noncompressed configuration, it should be understood that a variety of suitable materials may be used which are compressible to the compressed configuration as discussed herein according to the invention.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inch (0.064 to 0.10 cm), usually about 0.037 inch (0.094 cm), the wall thickness of the outer tubular member 14 can vary from about 0.002 to about 0.008 inch (0.0051 to 0.02 cm), typically about 0.003 to 0.005 inch (0.0076 to 0.013 cm). The inner tubular member 16 typically has an inner diameter of about 0.01 to about 0.018 inch (0.025 to 0.046 cm), usually about 0.016 inch (0.04 cm), and wall thickness of 0.004 to 0.008 inch (0.01 to 0.02 cm). The overall length of the catheter 10 may range from about 100 to about 150 cm, and is typically about 135 cm. Preferably, balloon 24 may have a length about 0.5 cm to about 4 cm and typically about 2 cm, and an inflated working diameter of about 1 to about 8 mm, and in a preferred embodiment, an uninflated diameter of not greater than about 1.3 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined by heat bonding or use of adhesives.

While the present invention is described herein in terms of certain preferred embodiments, those skilled in the art will recognize that various modifications and improvements may be made to the invention without departing from the scope thereof. For example, in the embodiment illustrated in FIG. 1, the catheter is over-the-wire stent delivery catheter. However, one of skill in the art will readily recognize that the balloons of this invention may also be used with other types of intravascular catheters, such as and rapid exchange dilatation catheters having a distal guidewire port and a proximal guidewire port and a short guidewire lumen extending between the proximal and distal guidewire ports in a distal section of the catheter. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

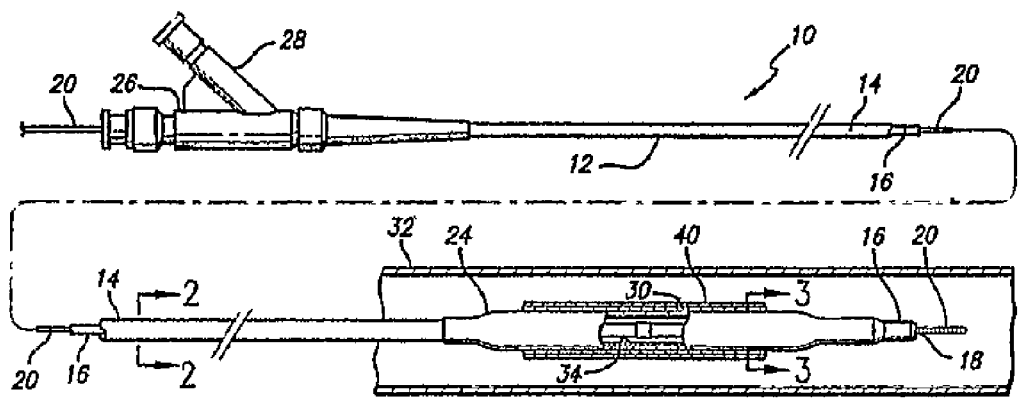

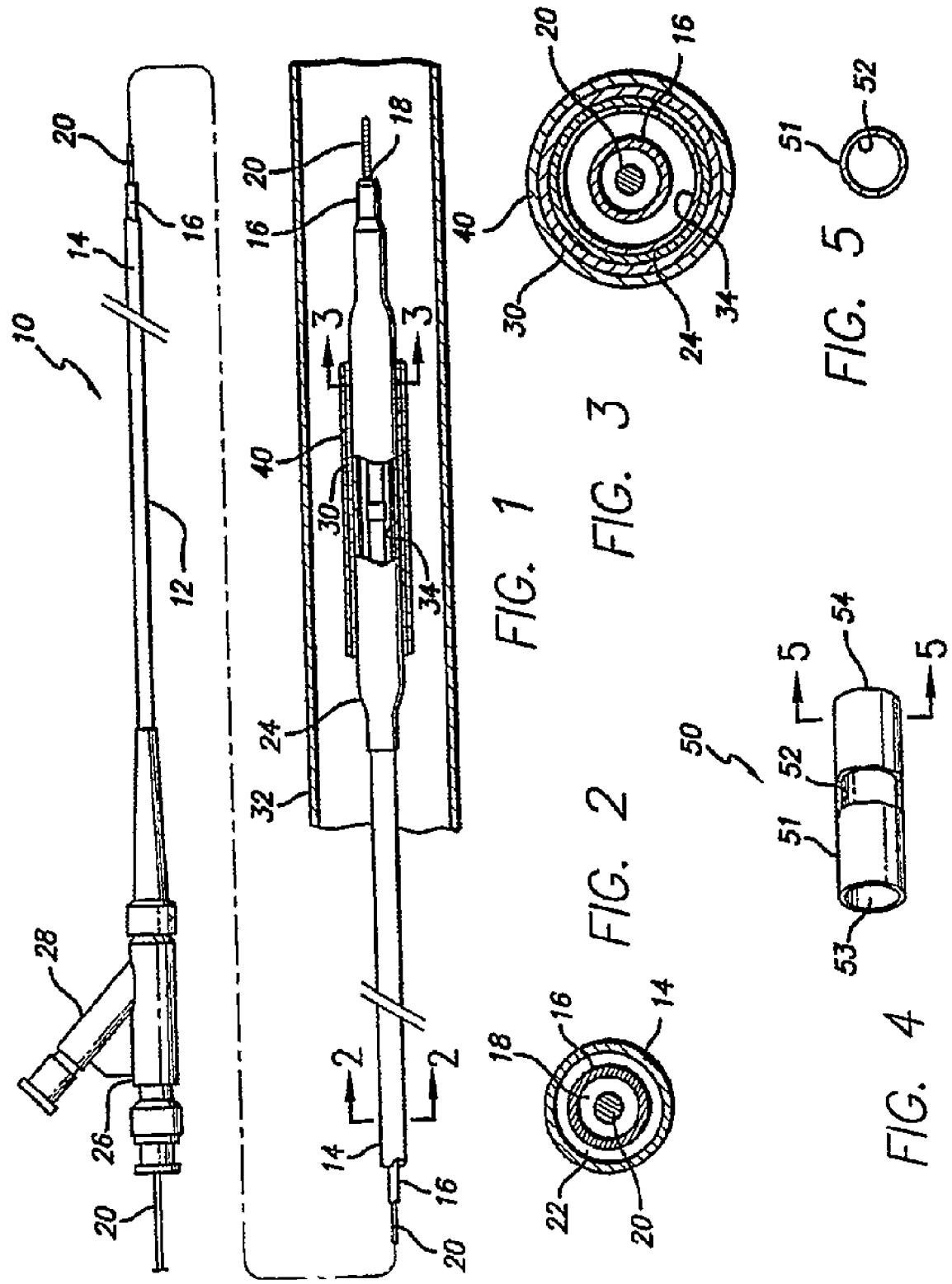

What is claimed is:

1. A method of forming a radially expandable component of a medical device, comprising
    a) helically wrapping polymeric material having a node and fibril structure, and fusing the helically wrapped material together to form a tube of the polymeric material; and
    b) heating the polymeric material tube to an elevated temperature, and axially compressing the polymeric material tube at the elevated temperature along a longitudinal axis of the tube to form the radially expandable component.

2. A method for forming a balloon for an intraluminal catheter, comprising
    a) compacting an ultrahigh molecular weight polyolefin;
    b) deforming the compacted polyolefin to render the polyolefin microporous and to impart a node and fibril microstructure to the polyolefin;
    c) forming a balloon by wrapping the deformed polyolefin around a mandrel to form a tube and heat fusing the wrapped polyolefin while substantially maintaining the oriented node and fibril structure; and
    d) reducing the porosity of the microporous polyolefin of the heat fused tube, to form a reduced porosity polyolefin having the node and fibril microstructure.

3. The method of claim 2 wherein the porosity of the microporous polyolefin is reduced by compressing the microporous polyolefin to form compressed polyolefin having a node and fibril microstructure.

4. The method of claim 3 including, before or after compression of the microporous polyolefin, forming a tubular member from the microporous polyolefin.

5. The method of claim 3 wherein the microporous polyolefin has a thickness, and compressing the microporous polyolefin comprises reducing the thickness of the microporous polyolefin.

6. The method of claim 5 wherein the thickness is reduced by 10% to 50%.

7. The method of claim 3 wherein the compacted polyolefin is deformed by stretching in at least one direction, and the porosity of the microporous polyolefin is reduced by compressing the microporous polyolefin in a direction substantially perpendicular to the at least one direction of stretching.

8. The method of claim 7 wherein the microporous polyolefin has a thickness, and compressing the microporous polyolefin further comprises restraining the thickness from increasing.

9. The method of claim 3 wherein the compacted polyolefin is deformed by stretching in at least one direction, and the porosity of the microporous polyolefin is reduced by compressing the microporous polyolefin in a direction substantially parallel to the at least one direction of stretching.

10. The method of claim 3 wherein the microporous polyolefin has a length, and compressing the microporous polyolefin comprises reducing the length of the microporous polyolefin.

11. The method of claim 10 wherein the length is reduced by 10% to 50%.

12. The method of claim 2 wherein the polyolefin is polyethylene and including, after heat fusing the wrapped polyethylene, axially compressing the tube along a longitudinal axis of the tube.

* * * * *

UNITED STATES PATENT AND TRADEMARK OFFICE
CERTIFICATE OF CORRECTION

PATENT NO. : 6,890,395 B2  Page 1 of 3
APPLICATION NO. : 10/438525
DATED : May 10, 2005
INVENTOR(S) : Murthy V. Simhambhatla It is certified that error appears in the above-identified patent and that said Letters Patent is hereby corrected as shown below:

Title Page,
Item (54), delete "MEDICAL DEVICE FORMED OF ULTRAHIGH MOLECULAR WEIGHT POLYOLEFIN" and insert --PROCESS OF MAKING A RADIALLY EXPANDABLE COMPONENT OF A MEDICAL DEVICE--.

The Title page drawing should be replaced with attached Figure 1 drawing.

The sheet of drawings consisting of figures 1-5 should be deleted as per attached figures 1-5.

Column 1,
Line 21, delete "an dilatation" and insert --a dilatation--.

Signed and Sealed this

Second Day of January, 2007

JON W. DUDAS
*Director of the United States Patent and Trademark Office*

(12) United States Patent
Simhambhatla

(10) Patent No.: US 6,890,395 B2
(45) Date of Patent: May 10, 2005

(54) MEDICAL DEVICE FORMED OF ULTRAHIGH MOLECULAR WEIGHT POLYOLEFIN

(75) Inventor: Murthy V. Simhambhatla, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 10/438,525

(22) Filed: May 15, 2003

(65) Prior Publication Data

US 2003/0194520 A1 Oct. 16, 2003

Related U.S. Application Data

(60) Division of application No. 09/713,642, filed on Nov. 14, 2000, now Pat. No. 6,602,224, which is a continuation-in-part of application No. 09/470,056, filed on Dec. 22, 1999, now Pat. No. 6,428,506.

(51) Int. Cl.$^7$ .................. B29C 47/88; B29C 53/40; B29C 53/42
(52) U.S. Cl. .................. 156/218; 264/127; 264/291; 264/323; 264/345
(58) Field of Search .................. 156/218; 264/127, 264/291, 323, 345

(56) References Cited

U.S. PATENT DOCUMENTS

| | | |
|---|---|---|
| 3,426,754 A | 2/1969 | Bierenbaum et al. |
| 3,679,538 A | 7/1972 | Druin et al. |
| 3,953,566 A | 4/1976 | Gore |
| 3,962,153 A | 5/1976 | Gore |
| 4,187,390 A | 2/1980 | Gore |
| 4,279,245 A | 7/1981 | Takagi et al. |

(Continued)

FOREIGN PATENT DOCUMENTS

| | | |
|---|---|---|
| EP | 0 253 513 | 1/1988 |
| EP | 0 267 719 | 5/1988 |
| EP | 0 313 263 | 4/1989 |
| EP | 0 376 503 | 7/1990 |
| WO | WO 91/01210 | 2/1991 |
| WO | WO 91/01210 | 2/1991 |

OTHER PUBLICATIONS

Keller, A., *Unusual Orientation Phenomena in Polyethylene Interpreted in Terms of the Morphology*, Journal of Polymer Science, vol. XV, pp. 31–49, 1955.
Breslow et al. "Soluble Catalysts for Ethylene Polymerization" J. Am. Chem. Soc. 81:81–86 (1959).
Hill, M.J., et al. *Direct Evidence for Distinctive, Stress–Induced Nucleus Crystals in the Crystallization of Oriented Polymer Melts*, Journal of Micromolecular Science, pp. 153–169, Mar. 1969.
Sprague, B.S., *Relationship of Structure and Morphology to Properties of "Hard" Elastic Fibers and Films*, Journal of Macromolecular Science, vol. B8(1–2), pp. 157–187, 1973.
van Hutten, P.F. et al., *Shish–Kebab as an Intermediate Morphology in Gel–Spinning/Hot–Drawing of Polyethylene*, Polymer Communications, vol. 24, pp. 237–240, 1983.

(Continued)

Primary Examiner—Sharon Kennedy
(74) Attorney, Agent, or Firm—Fulwider, Patton, Lee & Utecht LLP

(57) ABSTRACT

Medical devices having at least a component, such as a catheter balloon, stent cover and vascular graft, formed of ultrahigh molecular weight polyolefin, such as ultrahigh molecular weight polyethylene. The device component is formed from ultrahigh molecular weight polyethylene that has been processed so that it is microporous and has an oriented node and fibril structure. The device component expands compliantly at low strains and are substantially less compliant at higher strains. The invention also comprises methods for making such medical devices, including the steps of compacting a polyethylene powder and deforming it to impart the oriented structure.

12 Claims, 1 Drawing Sheet